United States Patent
Ro et al.

(10) Patent No.: US 7,670,842 B2
(45) Date of Patent: Mar. 2, 2010

(54) METHOD FOR DISCRIMINATING ORGANIC AGRICULTURAL PRODUCTS FROM CONVENTIONAL AGRICULTURAL PRODUCTS BY USING NITROGEN ISOTOPE INDEX

(75) Inventors: Hee Myong Ro, 2-105 Bando Apt., Ichon-1-dong, Yongsan-gu, Seoul (KR) 140-031; Woo Jung Choi, Suwon (KR)

(73) Assignee: Hee Myong Ro, Seoul (KR)

( * ) Notice: Subject to any disclaimer, the term of this patent is extended or adjusted under 35 U.S.C. 154(b) by 967 days.

(21) Appl. No.: 10/510,749

(22) PCT Filed: Apr. 12, 2003

(86) PCT No.: PCT/KR03/00740

§ 371 (c)(1),
(2), (4) Date: Oct. 12, 2004

(87) PCT Pub. No.: WO03/087813

PCT Pub. Date: Oct. 23, 2003

(65) Prior Publication Data

US 2005/0158871 A1    Jul. 21, 2005

(30) Foreign Application Priority Data

Apr. 12, 2002    (KR) .................... 10-2002-0019956

(51) Int. Cl.
*G01N 33/00* (2006.01)

(52) U.S. Cl. .................... 436/106; 436/100; 436/109; 436/110; 436/114; 436/173

(58) Field of Classification Search .................. 436/100, 436/106, 109, 110, 114, 173
See application file for complete search history.

(56) References Cited

FOREIGN PATENT DOCUMENTS

WO    WO 0140795 A2 *    6/2001

OTHER PUBLICATIONS

Yoneyama, Tadakatsu, Variation of Natural 15N Abundance of Crops and Soils in Japan with Special Reference to the Effect of Soil Conditions and Fertilizer Application, Soil Sci. Plant Nutr., 36(4), 667-675, 1990.*
Forstel, H., 15N/14N Ratio as a Tool to Study the Nitrogen Turnover in Vineyards, Isotopes in Environmental and Health Studies, 35 (4), 294, 1999.*
Choi et al, "Corn uptake and microbial immobilization of 15N-labeled urea-N in soil as affected by composted pig manure", 2001, Plant and Soil, 235: p. 1-9.*
Journal of Hydrology, vol. 42: 147-170, 1979 (Kretler, C.W.).
Soil Science vol. 118(5):308-316, 1974 (Shearer, G.B., et al.).

* cited by examiner

*Primary Examiner*—Lyle A Alexander
*Assistant Examiner*—Dennis M White
(74) *Attorney, Agent, or Firm*—Rothwell, Figg, Ernst & Manbeck, PC (57) ABSTRACT

The present invention provides a method for discriminating an organic farmland from a conventional farmland, comprising; (a) measuring an amount of nitrogen isotope in a soil sample of a farmland; (b) calculating a nitrogen isotope index according to the formula (I) using the resultant nitrogen isotope value and (c) determining whether the farmland belongs to an organic farmland or a conventional farmland. According to the present invention, it is possible to objectively discriminate an organic farmland from a conventional farmland or discriminate an organic crop from a conventional crop.

3 Claims, 5 Drawing Sheets

METHOD FOR DISCRIMINATING ORGANIC AGRICULTURAL PRODUCTS FROM CONVENTIONAL AGRICULTURAL PRODUCTS BY USING NITROGEN ISOTOPE INDEX

CROSS REFERENCE TO RELATED APPLICATION

This application is a 35 U.S.C. § 371 National Phase Entry Application from PCT/KR03/100740, filed Apr. 12, 2003, and designating the U.S.

BACKGROUND OF THE INVENTION

1. Field of the Invention

The present invention relates to a method for discriminating an organic crop from a conventional crop, or an organic farmland from a conventional farmland by using a nitrogen isotope index in a soil sample or crop sample.

2. Description of the Related Art

In conventional cultivation practice, an excess amount of chemical fertilizer and pesticides have been used to increase the production yield. However, those chemical fertilizer and pesticides have caused ecological disturbance such as accumulation of salts and imbalance of nutrients in soil, decrease in the number of soil microorganisms and natural predators; water contamination; and safety problems in agricultural products, etc. With respect to these problems, it is anticipated that international trade volume in organic crop will be increased by way of international efforts to link agriculture, environment and trade, and thus to make international regulations to resolve the above problems. Further, a standard for an organic crop will be set up in Codex. OECD is planning to evaluate agricultural policies of each country by developing environmental index of agriculture in 13 divisions.

In response to these international efforts, "Law for promoting environmentally favorable agriculture" and "enforcement Law thereof" have been made in Korea to promote agriculture in an environmentally favorable way and to promote the production of value-added agricultural products by introducing a quality certification system therefor. According to the standard adopted in the quality certification system for environmentally favorable agricultural products, i.e., Quality Standard for crop (Korea), agricultural products are classified into four categories: low-pesticide agricultural products (the amount of used synthesized pesticide is ½ or lower of the standard amount thereof and the amount of used chemical fertilizer is ½ or lower of the recommended amount thereof); pesticide free agricultural products (no use of synthesized pesticides and the amount of used chemical fertilizer is ⅓ or lower of the recommended amount thereof); transitional organic agricultural products (no use of synthesized pesticides more than 1 year and no use of chemical fertilizer); and organic agricultural products (no use of synthesized pesticides more than 3 years and no use of chemical fertilizer). Thus, it is critical to determine whether a synthesized pesticide or a chemical fertilizer has been used or not in evaluating agricultural products according to the quality certification system.

Synthesized pesticides can be investigated by monitoring residual pesticides in a crop or soil sample. On the contrary, chemical fertilizer can be investigated only by an indirect method such as data on farming and an analysis of chemical properties of corresponding soil. However, there were problems that data on farming may be arbitrarily made by a farmer, and although the chemical properties of soil are directly affected by the application rates of fertilizers thereto, there is no scientific relationship between the chemical properties of soil and a type of fertilizer (chemical fertilizer or organic fertilizer) applied thereto. According to the state of the art, it is impossible to objectively determine whether a chemical fertilizer or an organic fertilizer has been used in a soil. Thus, there is a need for a method for determining whether chemical fertilizer or organic fertilizer has been used in soil of interest. Such a method is also needed to satisfy the consumer's need to know whether an agricultural product of interest was grown with chemical fertilizer or organic fertilizer.

There has been an attempt to determine the source of water contamination on the basis that a nitrogen isotope ratio of chemical fertilizer is different from that of livestock manure (Kohl et al, 1971, Fertilizer nitrogen: contribution to nitrate in surface water in a corn belt watershed, *Science* 174: 1331-1334). An analysis for the nitrogen isotope was employed for the purpose of studying the source of water contamination (Iqbal et al, 1997, Nitrogen isotope indicators of seasonal source variability to groundwater, *Environmental Geology* 32: 210-218). However, the analysis for nitrogen isotope has never been used to investigate the kind of fertilizer (chemical vs. organic) applied to a farmland or to discriminate a crop grown with organic fertilizer from a crop grown with a chemical fertilizer.

The inventors have statistically analyzed distribution of nitrogen isotope in chemical fertilizer and organic fertilizer, and carried out experiments to examine the effect of chemical fertilizer or organic fertilizer on the nitrogen isotope index of a soil and a crop therefrom, and completed the present invention.

SUMMARY OF THE INVENTION

The present invention provides a method for discriminating an organic farmland from a conventional farmland.

The present invention provides a method for discriminating an organic crop from a conventional crop.

The present invention provides a method for discriminating an organic crop from a conventional crop or an organic farmland from a conventional farmland.

In one aspect, the present invention provides a method for discriminating an organic farmland from a conventional farmland, comprising;

(a) measuring an amount of nitrogen isotope in a soil sample of a farmland;

(b) calculating a nitrogen isotope index according to the formula (I) using the obtained nitrogen isotope value:

$$\delta^{15}N = [R \text{ sample}/R \text{ reference} - 1] \times 1{,}000 \qquad (I)$$

wherein $\delta^{15}N$ is a nitrogen isotope index, R sample and R reference are $^{15}N/(^{15}N+^{14}N)$ ratio of sample and reference, respectively; and (c) determining whether a farmland belongs to a organic farmland or a conventional farmland.

In one aspect, the present invention also provides a method for discriminating an organic crop from a conventional crop, comprising;

(a) measuring an amount of nitrogen isotope in a crop sample;

(b) calculating a nitrogen isotope index according to the formula (I) using the obtained nitrogen isotope value:

$$\delta^{15}N = [R \text{ sample}/R \text{ reference} - 1] \times 1{,}000 \qquad (I)$$

wherein $\delta^{15}N$ is a nitrogen isotope index, R sample and R reference are $^{15}N/(^{15}N+^{14}N)$ ratio of sample and reference, respectively; and (c) determining whether a crop belongs to a organic crop or a conventional crop.

The terms, as used herein, are referred to as follows otherwise mentioned. The term "nitrogen isotope" refers to nitrogen isotopes including $^{15}N$ and $^{14}N$. The term "nitrogen isotope ratio" refers to a ratio of heavy nitrogen ($^{15}N$) to total nitrogen ($^{15}N+^{14}N$), i.e., represented by $^{15}N/(^{15}N+^{14}N)$. Further, the term "nitrogen isotope index($\delta^{15}N$)(‰)" of a sample refers to a normalized index of a nitrogen isotope ratio of a sample to that of a reference sample defined as following formula (I):

$$\delta^{15}N = [R\ \text{sample}/R\ \text{reference} - 1] \times 1,000 \tag{I}$$

wherein $\delta^{15}N$ is a nitrogen isotope index, R sample and R reference are $15N/(^{15}N+^{14}N)$ ratio of sample and reference, respectively.

Figure 1:
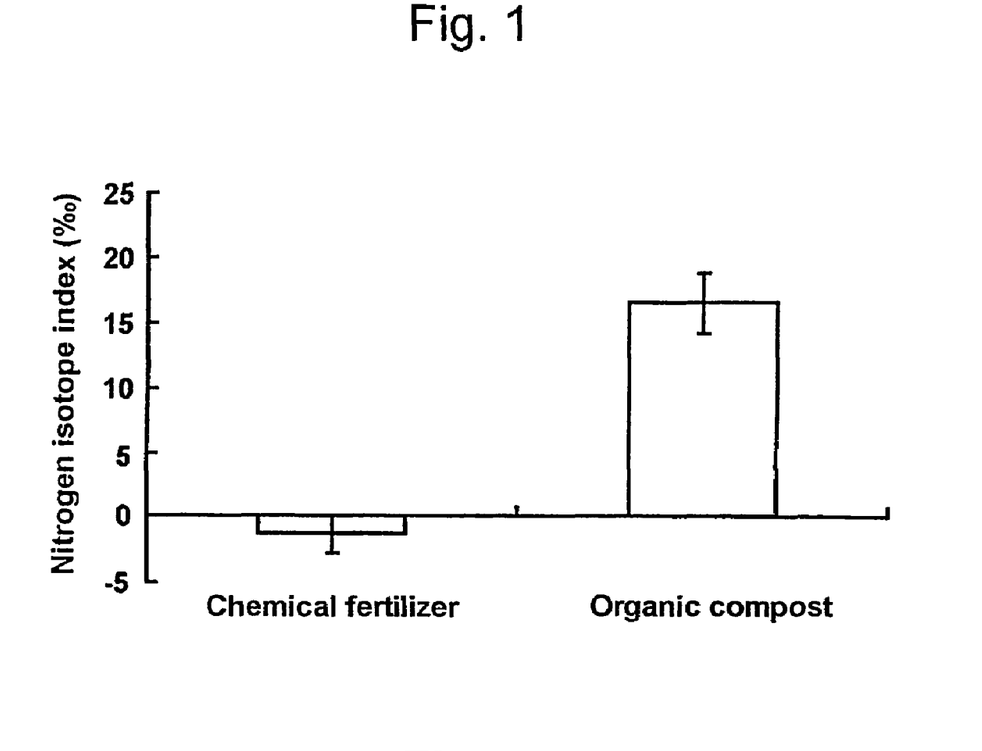
FIG. 1 illustrates average nitrogen isotope index values for 8 types of chemical fertilizers and 27 types of organic compost fertilizers which are commercially available in Korea.

Atmospheric nitrogen ($N_2$) is typically used as reference material. In this case, the $\delta^{15}N$ value for atmospheric nitrogen is 0‰ by definition. The higher level of nitrogen isotope index means higher level of $^{15}N$ in a sample. Typically, a nitrogen isotope index of an organic fertilizer is higher than that of a chemical fertilizer. FIG. 1 illustrates average of the nitrogen isotope index for 8 types of chemical fertilizers and 27 types of organic fertilizers, which are commercially available in Korea. As shown in FIG. 1, the average nitrogen isotope index for organic fertilizers (16.7±2.3‰) is higher than that of chemical fertilizers (−1.5±1.50‰). The present invention is made based on such differences in the nitrogen isotope index between chemical fertilizer and organic fertilizer.

Moreover, the term "organic farmland", as used herein, generally refers to a farmland to which an organic fertilizer has been applied for a certain period. An organic farmland includes a farmland to which an organic fertilizer has been applied as a sole fertilizer source or as a substantially major fertilizer for a certain period. The term "organic crop" generally refers to a crop that harvested after having been grown by using organic fertilizer and includes an organic crop and transitional organic crop under Quality Standard for crop (Korea). However, the terms "organic farmland" and "organic crop" are not intended to be limited to the above mentioned meaning since the exact meanings of "organic farmland" and "organic crop" can be defined by assigning a specific nitrogen isotope index values at a specific application of the present invention.

The term "organic fertilizer" refers to a fertilizer produced by processing a biological materials such as animal manures and plants materials, and includes both an organic fertilizer and byproducts fertilizer under Official Standard for fertilizers (Korea). Urea can be classified as an organic fertilizer if it is derived from an organism, while it can not be classified as an organic fertilizer if it is produced by a synthesis through a chemical engineering process.

The term "conventional cultivation" refers to a type of cultivation using a chemical fertilizer, which is a typical type of cultivation. The term "conventional farmland", as used herein, generally refers to a type of farmland to which chemical fertilizer has been applied as a sole fertilizer source or as a substantially major fertilizer for a certain period. The term "conventional crop" generally refers to a crop that harvested after having been grown by using a chemical fertilizer. However, the terms "conventional farmland" and "conventional crop" are not intended to be limited to the above mentioned meaning since the exact meanings of "conventional farmland" and "conventional crop" can be defined by assigning a specific nitrogen isotope index values at a specific application of the present invention.

In step (a) of the present method, the measurement of the amount of a nitrogen isotope may be achieved by using a conventional apparatus which is used in the art, such as a stable isotope ratio mass spectrometer. The soil sample for the measurement of the nitrogen isotope amount may be prepared from the whole soil or by selecting a portion thereof having a specific range of particle size. Further, the amount of nitrogen isotope of the soil sample may be measured for whole nitrogen including ammonium($NH_4^+$) nitrogen, nitrate($NO_3^-$) nitrogen and organic nitrogen, as well as for the foregoing each component.

The present invention may be applied to the crops, for examples, but not limited to, a leaf vegetables such as a Chinese cabbage, greens for pickling, a *Brassica campestris* (a Chinese spinach-like green vegetable), a cabbage, a cauliflower, a broccoli, a Brussels sprout, an onion, a Welsh onion, a garlic, a scallion, a leek, an asparagus, a lettuce, a green for salad (which is called Saladana in Japan), a celery, a spinach, a crown daisy, a parsley, a trefoil (which is called Mitsuba in Japan and is useful as herb), a dropwort, an udo (which is an *Aralia cordata*), a Japanese ginger, a Japanese butterbur and a labiate; a fruit vegetables such as a cucumber, a pumpkins, a water melon, a melon, a tomato, an eggplant, a pimento, a strawberry, a kidney bean, a broad bean, a pea, a soybean and a corn; and a root vegetables such as a radish, a turnip, a burdock, a carrot, a potato, a taro, a sweet potato, a ginger, and a lotus. Other crops to which the present invention can be applied, include a rice, a barley, a wheat and other flowery plants, but not limited to these examples. Preferably, the crops are a leaf vegetables such as a Chinese cabbage, greens for pickling, a *Brassica campestris* (a Chinese spinach-like green vegetable), a cabbage, a cauliflower, a broccoli, a Brussels sprout, an onion, a Welsh onion, a garlic, a scallion, a leek, an asparagus, a lettuce, a green for salad (which is called Saladana in Japan), a celery, a spinach, a crown daisy, a parsley, a trefoil (which is called Mitsuba in Japan and is useful as herb), a dropwort, an udo (which is an *Aralia cordata*), a Japanese ginger, a Japanese butterbur and a labiate. In step (c) of the present method, determination whether a farmland belongs to an organic farmland or a conventional farmland, or determination whether a crop belongs to an organic crop or a conventional crop can be achieved by comparing the obtained nitrogen isotope index in a sample of a farmland or a crop with that of reference farmland or crop sample.

In one embodiment of the present invention, the present invention provides a method for discriminating an organic farmland from a conventional farmland by using a nitrogen isotope index, comprising;
 (a) measuring an amount of a nitrogen isotope of whole nitrogen in a soil sample from a farmland;
 (b) calculating a nitrogen isotope index according to the formula (I) using the obtained nitrogen isotope value:

$$\delta^{15}N = [R\ \text{sample}/R\ \text{reference} - 1] \times 1,000 \tag{I}$$

wherein $\delta^{15}N$ is a nitrogen isotope index, R sample and R reference are $^{15}N/(^{15}N+^{14}N)$ ratio of sample and reference, respectively; and
 (c) determining whether a farmland belongs to an organic farmland or a conventional farmland.

In step (c), it is preferable that if the nitrogen isotope index is 5‰ or lower, the farmland is determined to be a conventional farmland, and if the nitrogen isotope index is 8‰ or higher, the farmland is determined to be an organic farmland. This criteria is based on a fact that the nitrogen isotope index for a conventional farmland to which chemical fertilizer had been applied was about 5.9±0.7‰, and an organic farmland to which an organic fertilizer had been applied was 8.8±0.9‰ (see FIG. 2). However, it is not intended to limit the scope of the present invention to this specific criteria, since the nitrogen isotope index may be dependent on the type of soil, type of organic fertilizer and the duration of organic cultivation, etc. In another embodiment of the present invention, the present invention provides a method for discriminating an organic farmland from a conventional farmland by using a nitrogen isotope index, comprising;

(a) measuring an amount of a nitrogen isotope of nitrate ($NO_3^-$) in a soil sample of a farmland;
(b) calculating a nitrogen isotope index according to the formula (I) using the obtained nitrogen isotope value:

$$\delta^{15}N = [R \text{ sample}/R \text{ reference} - 1] \times 1,000 \quad (I)$$

wherein $\delta^{15}N$ is a nitrogen isotope index, R sample and R reference are $^{15}N/(^{15}N+^{14}N)$ ratio of sample and reference, respectively; and
(c) determining whether a farmland belongs to an organic farmland or a conventional farmland.

In step (c), it is preferable that if the nitrogen isotope index is 4‰ or lower, the farmland is determined to be a conventional farmland, and if the nitrogen isotope index is 7 or higher, the farmland is determined to be an organic farmland. These criteria are based on a fact that the nitrogen isotope index for a conventionally cultivated farmland to which a chemical fertilizer had been applied was about 4.7±1.1‰, and an organic farmland to which an organic fertilizer had been applied was 11.6±4.5‰ (see FIG. 3). However, it is not intended to limit the scope of the present invention to this specific criteria, since the nitrogen isotope index may be dependent on the type of soil, type of organic fertilizer and the duration of organic cultivation, etc.

In yet another embodiment of the present invention, the present invention provides a method for discriminating an organic crop from a conventional crop by using a nitrogen isotope index, comprising;

(a) measuring an amount of a nitrogen isotope of whole nitrogen in a crop sample harvested from a farmland;
(b) calculating a nitrogen isotope index according to the formula (I) using the obtained nitrogen isotope index:

$$\delta^{15}N = [R \text{ sample}/R \text{ reference} - 1] \times 1,000 \quad (I)$$

wherein $\delta^{15}N$ is a nitrogen isotope index, R sample and R reference are $^{15}N/(^{15}N+^{14}N)$ ratio of sample and reference, respectively; and
(c) determining whether a crop belongs to an organic crop or a conventional crop.

Figure 4:
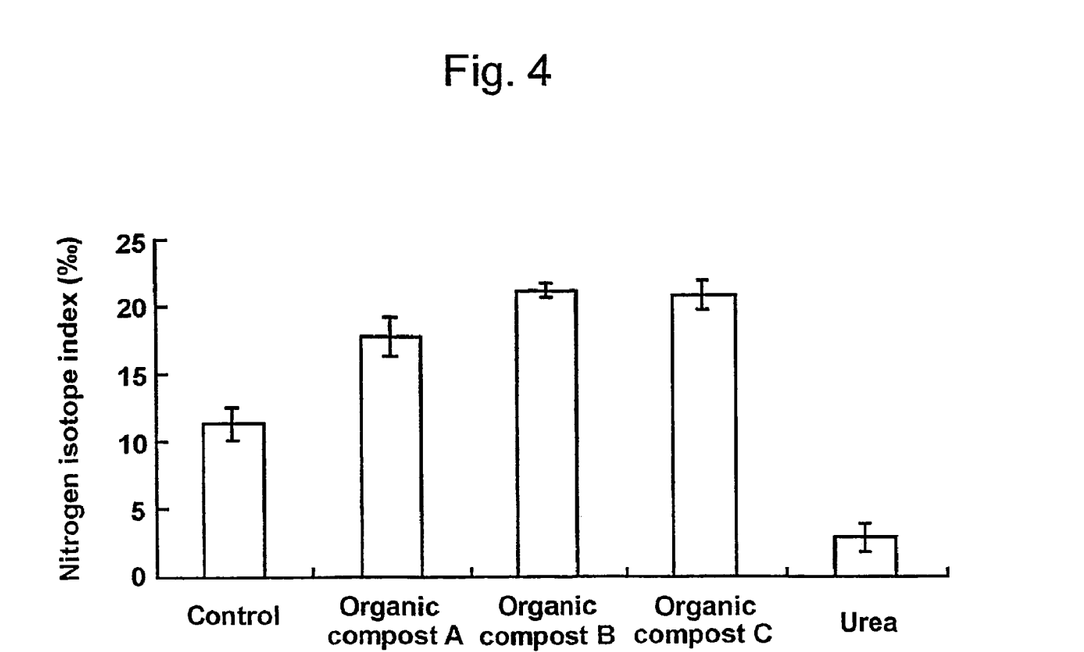
FIG. 4 illustrates nitrogen isotope index values of whole nitrogen in a Chinese cabbage sample which has been grown with an organic compost or a chemical fertilizer, respectively.
Figure 5:
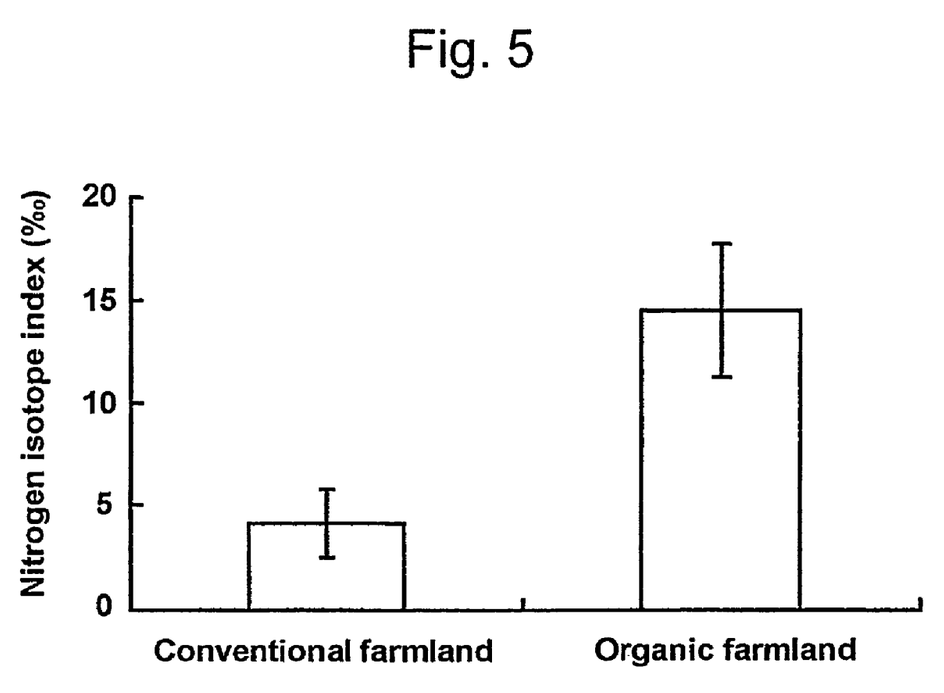
FIG. 5 illustrates nitrogen isotope index values of crop samples (a Chinese cabbage, a lettuce, a spinach, a sesame, a cucumber, a eggplant, a red pepper, a cabbage, a *Perilla japonica*) which have been grown in a organic farmland or conventional farmland, respectively.

In step (c), it is preferable that if the nitrogen isotope index is 3‰ or lower, the crop is determined to be a conventional crop, and if the nitrogen isotope index is 8‰ or higher, the crop is determined to be an organic crop (see FIG. 4 and FIG. 5). A preferable crop includes, but not limited to, a leaf vegetables such as a Chinese cabbage, greens for pickling, a *Brassica campestris* (a Chinese spinach-like green vegetable), a cabbage, a cauliflower, a broccoli, a Brussels sprout, an onion, a Welsh onion, a garlic, a scallion, a leek, an asparagus, a lettuce, a green for salad (which is called Saladana in Japan), a celery, a spinach, a crown daisy, a parsley, a trefoil (which is called Mitsuba in Japan and is useful as herb), a dropwort, an udo (which is an *Aralia cordata*), a Japanese ginger, a Japanese butterbur and a labiate. However, it is not intended to limit the scope of the present invention to this specific criteria, since the range of the nitrogen isotope index may be dependent on the type of soil, a type of an organic fertilizer and the duration of organic cultivation, etc.

Moreover, in another embodiment of the present invention, the present invention provides a method for discriminating an organic crop from a conventional crop, comprising;

(a) measuring an amount of nitrogen isotope in a crop sample during the cultivation period at appropriate intervals;
(b) calculating a pattern of nitrogen isotope index according to the formula (I) using each of the obtained nitrogen isotope value:

$$\delta^{15}N = [R \text{ sample}/R \text{ reference} - 1] \times 1,000 \quad (I)$$

wherein $\delta^{15}N$ is a nitrogen isotope index, R sample and R reference are $^{15}N/(^{15}N+^{14}N)$ ratio of sample and reference, respectively; and
(c) determining whether a crop belongs to a organic crop or a conventional crop:

In step (a) of the present method, the amount of nitrogen isotope for a crop is a measured during cultivation period of the crop at appropriate intervals. In this way, a nitrogen isotope fluctuation patterns can be obtained by measuring the amount of nitrogen isotope.

In step (c) of the present method, it is preferable that if the nitrogen isotope index exhibits an increasing trend during cultivation period, the crop is determined to be a conventional crop during the cultivation of which a chemical fertilizer was used as a sole fertilizer source in the early growth period; if the nitrogen isotope index exhibits a decreasing trend after initial increasing trend during the cultivation, the crop is determined to be a conventional crop during the cultivation of which a chemical fertilizer was used separately as a basal fertilizer in the early growth period and as an additional fertilizer in the latter growth period; if the nitrogen isotope index exhibits almost no fluctuations or a slight decreasing trend during cultivation period, the crop is determined to be an organic crop during the cultivation of which an organic fertilizer was used as a sole fertilizer; and if the nitrogen isotope index exhibits a decreasing trend after initial no fluctuation during cultivation period, the crop is determined to be a conventional crop during the cultivation of which an organic fertilizer was used as a basal fertilizer in the early growth period and a chemical fertilizer was used as an additional fertilizer. These criteria are based on a result of experiment on the fluctuation pattern of nitrogen index of a crop grown with a chemical or organic fertilizer during cultivation (see FIG. 6). However, it is not intended to limit the scope of the present invention to this specific criteria, since the range of the nitrogen isotope index may be dependent on the type of soil, a type of an organic fertilizer and the duration of organic cultivation, etc.

In another embodiment, the present invention provides a method for discriminating an organic crop from a conventional crop or an organic farmland from a conventional farmland, comprising;

(a) measuring an amount of nitrogen isotope in a soil sample of a farmland and a crop sample harvested therefrom;
(b) calculating a nitrogen isotope index according to the formula (I) using each of the nitrogen isotope value:

$$\delta^{15}N = [R \text{ sample}/R \text{ reference} - 1] \times 1,000 \quad (I)$$

wherein $\delta^{15}N$ is a nitrogen isotope index, R sample and R reference are $^{15}N/(^{15}N+^{14}N)$ ratio of sample and reference, respectively; and
(c) comparing the resultant nitrogen isotope index values of the soil with those of the crop to determine whether the farmland belongs to an organic farmland or a conventional farmland, or to determine whether the crop from the farmland belongs to an organic crop or a conventional crop.

In step (a) of the invention, the nitrogen isotope amount of the soil sample or a crop sample may be measured for a portion of the whole nitrogen including ammonium($NH_4^+$) nitrogen, nitrate($NO_3^-$) nitrogen and an organic nitrogen, as well as the whole nitrogen.

In step (c) of the present method, it is preferable that if the nitrogen isotope index value of the crop is lower than the nitrogen isotope index value of the soil, the crop is determined to be a conventional crop or the farmland is determined to be a conventional farmland; if the nitrogen isotope index value of the crop is higher than the nitrogen isotope index value of the soil, the crop is determined to be an organic crop or the farmland is determined to be an organic farmland. These criteria are based on a result of an experiment on a relationship between the nitrogen isotope index of a soil sample and that of a crop sample therefrom (see FIG. 7). However, it is not intended to limit the scope of the present invention to this specific criteria, since the range of the nitrogen isotope index may be dependent on the type of soil, a type of an organic fertilizer and the duration of organic cultivation, etc.

The above-mentioned embodiment of the present invention can be used in combination to provide a more reliable method for discriminating an organic farmland from a conventional farmland or an organic crop from a conventional crop. For example, the method for discriminating an organic farmland from a conventional farmland and the method for discriminating an organic crop from a conventional crop, wherein the crop is harvested from the farmland, can be used in combination. Thus, reliability of both the methods can be secured since if the farmland where a crop has been grown has been determined to be an organic farmland, the crop harvested therefrom would be most likely an organic crop; On the contrary, if the crop has been determined to be an organic crop, the farmland where the crop harvested therefrom would be most likely an organic farmland, thereby increasing a reliability of the method. The present invention includes any kind of combinations to increase the reliability of the method.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

The present invention will be described in greater detail with reference to the following examples. The following examples are for illustrative purposes and are not intended to limit the scope of the invention.

EXAMPLE 1

In this example, a nitrogen isotope amount has been measured and a nitrogen isotope index has been determined for 8 types of chemical fertilizers and 27 types of organic fertilizers which are commercially available in Korea.

The chemical fertilizers were urea, ammonium sulfate and 6 compound fertilizers, and the organic fertilizers were an organic fertilizer or byproducts fertilizer under Official Standard for fertilizers (Korea) including composted pig manure, composted chicken manure, and composted cow manure. The nitrogen isotope content and index were measured and determined by using a continous-flow stable isotope ratio mass spectrometer (IsoPrime-EA, Micromass, England) linked with a CN-analyzer (Limaux et al., 1999; Monaghan and Barraclough, 1995). The accuracy and reproducibility of the analysis method, which were checked with a reference material (RM 8548: IAEA-N2) obtained from International Atomic Energy Agency (IAEA), were better than 0.4% and 0.2%, respectively.

FIG. 1 illustrates average nitrogen isotope index values for 8 types of chemical fertilizers and 27 types of organic compost fertilizers which are commercially available in Korea. As shown in FIG. 1, the average nitrogen isotope index values for chemical fertilizers and organic fertilizers were −1.54±1.50‰ and 16.69±2.32‰, respectively. Thus, the average nitrogen isotope index values for the organic fertilizer was higher than those of the chemical fertilizer. The inventors have investigated whether these differences between the nitrogen isotope index values of the organic fertilizer and those of the chemical fertilizer can be applied to a soil and a crop, and successfully discriminated an organic crop from a conventional crop, or an organic farmland from a conventional farmland based on the nitrogen isotope index.

EXAMPLE 2

In this Example, a nitrogen isotope amount and index of whole nitrogen in a soil sample obtained from a conventional farmland to which a chemical fertilizer had been applied and an organic farmland to which an organic fertilizer had been applied, were measured and determined.

Urea and other chemical fertilizers had been applied to the conventional farmland for the last 20 years at rates of 200-400 $kgNha^{-1}Yr^{-1}$. A composted pig manure and other various organic fertilizers had been applied to the organic farmland for the last 5 years at rates of 300-600 $kgNha^{-1}Yr^{-1}$.

The soil sample was prepared from the surface layer (a soil layer which is located within in the depth of 0-15 cm from the surface). The nitrogen isotope index of whole soil nitrogen was measured and determined by using a continous-flow stable isotope ratio mass spectrometer (IsoPrime-EA, Micromass, England) linked with a CN-analyzer (Limaux et al., 1999; Monaghan and Barraclough, 1995). The accuracy and reproducibility of the analysis method, which were checked with a reference material (RM 8548: IAEA-N2) obtained from International Atomic Energy Agency (IAEA), were better than 0.4% and 0.2%, respectively.

Figure 2:
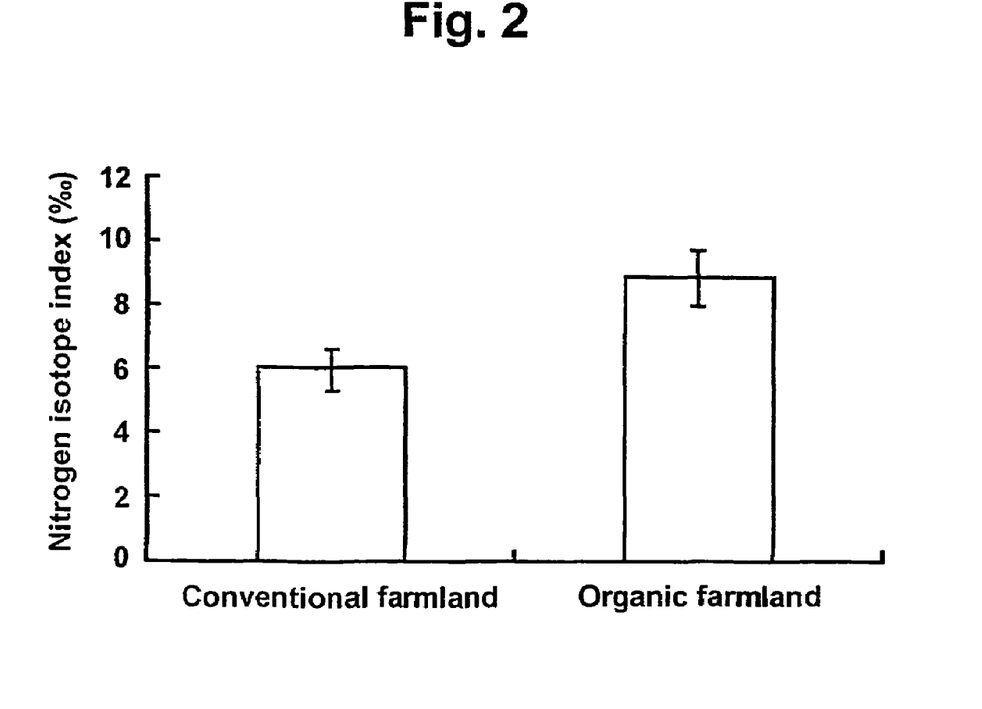
FIG. 2 illustrates nitrogen isotope index values for a soil sample from a conventional farmland and an organic farmland.

FIG. 2 illustrates nitrogen isotope index values of whole nitrogen for a conventional farmland and an organic farmland. As shown in FIG. 2, the nitrogen isotope index values for the conventional farmland and an organic farmland were 5.9±0.7‰ and 8.8±0.9‰, respectively. Thus, the experimentation results indicate that the nitrogen isotope index for a soil was increased by using an organic fertilizer having a higher nitrogen isotope index. Therefore, it was possible to discriminate an organic farmland from a conventional farmland. That is, if a nitrogen isotope index value in a soil sample is lower than 5‰, it may be determined to be a soil from a conventional farmland, and if a nitrogen isotope index value in a soil sample is 8‰ or higher, it may be determined to be a soil from a farmland.

EXAMPLE 3

In this Example, a nitrogen isotope amount and index of nitrate ($NO_3^-$) in a soil sample obtained from a conventional farmland to which a chemical fertilizer had been applied and an organic farmland to which an organic fertilizer had been applied, were measured and determined. The measurement and determination were carried out in the same way as in the Example 2 except that the types of nitrogen analysed was nitrate nitrogen.

Figure 3:
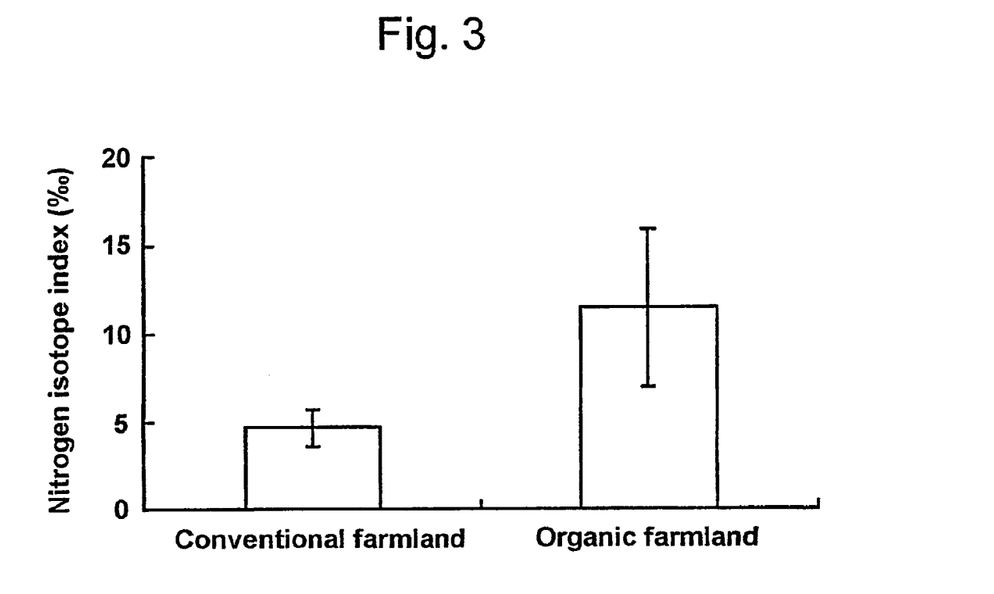
FIG. 3 illustrates nitrogen isotope index values of nitrate for a conventional farmland and an organic farmland.

FIG. 3 illustrates nitrogen isotope index values of nitrate for a conventional farmland and an organic farmland. As shown in FIG. 3, the nitrogen isotope index values for the conventional farmland and an organic farmland were 4.7±4.5‰ and 11.6±4.5‰, respectively. Thus, the results of this experiment indicate that the nitrogen isotope index of nitrate nitrogen in a soil was increased by using an organic fertilizer having a higher nitrogen isotope index. Therefore, it was possible to discriminate an organic farmland from a conventional farmland. That is, if a nitrogen isotope index value in a soil sample is 4‰ or lower, it may be determined to be a soil from a conventional farmland, and if a nitrogen isotope index value in a soil sample is 7‰ or higher, it may be determined to be a soil from the farmland.

EXAMPLE 4

In this Example, a nitrogen isotope index of a crop sample which had been grown with an organic fertilizer or a chemical fertilizer was measured. A nitrogen isotope index of a crop sample which had been grown in an organic farmland and a conventional farmland was also measured.

(1) Measurement of Nitrogen Isotope Index of a Crop Sample which had been Grown with an Organic Fertilizer or a Chemical Fertilizer To discriminate an organic crop from a conventionally cultivated crop by using a nitrogen isotope index of whole nitrogen, a crop had been grown in an identical soil environment with an organic fertilizer or a chemical fertilizer and then a nitrogen isotope index of whole nitrogen for the crop was measured.

The crop, a Chinese cabbage grown in the soil prepared from a conventional farmland was applied with about 500 kgNha$^{-1}$ of each fertilizer, and grown for about 70 days. The Chinese cabbage was harvested and the nitrogen isotope index was measured. To prepare a sample, a whole part of the harvested Chinese cabbage was dried at 60° C. and ground to a fine powder. The same apparatus for the analysis of a nitrogen isotope ratio as in Example 2 was used. As a control, a Chinese cabbage was grown and harvested without applying neither a chemical nor an organic fertilizer. An organic fertilizer A, B, and C were produced from Yongin Stock-Raiser's association, Kunwi Stock-Raiser's association, and Sambi Corporation by using various raw materials and a composting process, and urea produced by chemical synthesis was used as a chemical fertilizer.

FIG. 4 illustrates a nitrogen isotope index value of whole nitrogen in a Chinese cabbage sample which has been grown with an organic compost or a chemical fertilizer, respectively. As shown in FIG. 4, a nitrogen isotope index of a Chinese cabbage sample grown with organic fertilizer A, B, and C were 17.8±1.57‰, 21.2±0.6‰ and 20.8±1.1‰, respectively, and a nitrogen isotope index of the control was 11.3±1.2‰, and a nitrogen isotope index of the Chinese cabbage sample grown with a chemically synthesized urea was 3.0±1.1‰.

(2) Measurement of a Nitrogen Isotope Index of a Crop Sample Grown in an Organic Farmland or a Conventional Farmland.

A nitrogen isotope index of a crop which had been grown in an organic farmland or a conventional farmland was measured in the same way as in the Example 4 (1). The types of crops used in this Example were a Chinese cabbage, a lettuce, a spinach, a sesame, a cucumber, an eggplant, a red pepper, a cabbage and a *Perilla japonica*, and were grown in the range of 30-60 days in accordance with a crop. The organic farmland was a farmland which had been cultivated at least 5 years with various organic fertilizers at rates of 300-600 kgNha$^{-1}$Yr$^{-1}$, and the conventional farmland was a farmland which had been cultivated at least 20 years with chemical fertilizers (mainly urea) at rates of 200-400 kgNha$^{-1}$Yr$^{-1}$.

FIG. 5 illustrates nitrogen isotope index value for crop samples (a Chinese cabbage, a lettuce, a spinach, a sesame, a cucumber, an eggplant, a red pepper, a cabbage, a *Perilla japonica*) which had been grown in an organic farmland or conventional farmland, respectively. As shown in FIG. 5, a nitrogen iosotope index for a crop which had been grown in an organic farmland and a conventional farmland were 4.1±1.7‰ and 14.6±3.3‰, respectively.

In accordance with the Example 4 (1) and (2), it was possible to discriminate an organic crop from a conventional crop by measuring a nitrogen isotope index of a crop sample. That is, if a nitrogen isotope index value of a crop sample is 3‰ or lower, it may be determined to be a crop grown in a conventional farmland or with a chemical fertilizer, and if a nitrogen isotope index value for a crop sample is 8‰ or higher, it may be determined to be a crop grown in an organic farmland or with an organic fertilizer.

EXAMPLE 5

A nitrogen isotope ratio of a crop sample was measured during cultivation period. To this end, the crop was grown with a chemical fertilizer (urea) or an organic fertilizer (composted manure) and a sample was taken for the measurement at appropriate intervals during the cultivation period.

The crop used in this Example was a maize plant, grown with fertilizer at a rate of 150 kgNha$^{-1}$ (In case of split application, basal and additional fertilizer were applied at equal rate; 75 kgNha$^{-1}$ for each), and the nitrogen isotope ratio of the whole nitrogen was measured for a crop sample at the 30$^{th}$, 40$^{th}$ and 60$^{th}$ day after sowing. The measurement was carried out in the same way as in the Example 4(1).

Figure 6:
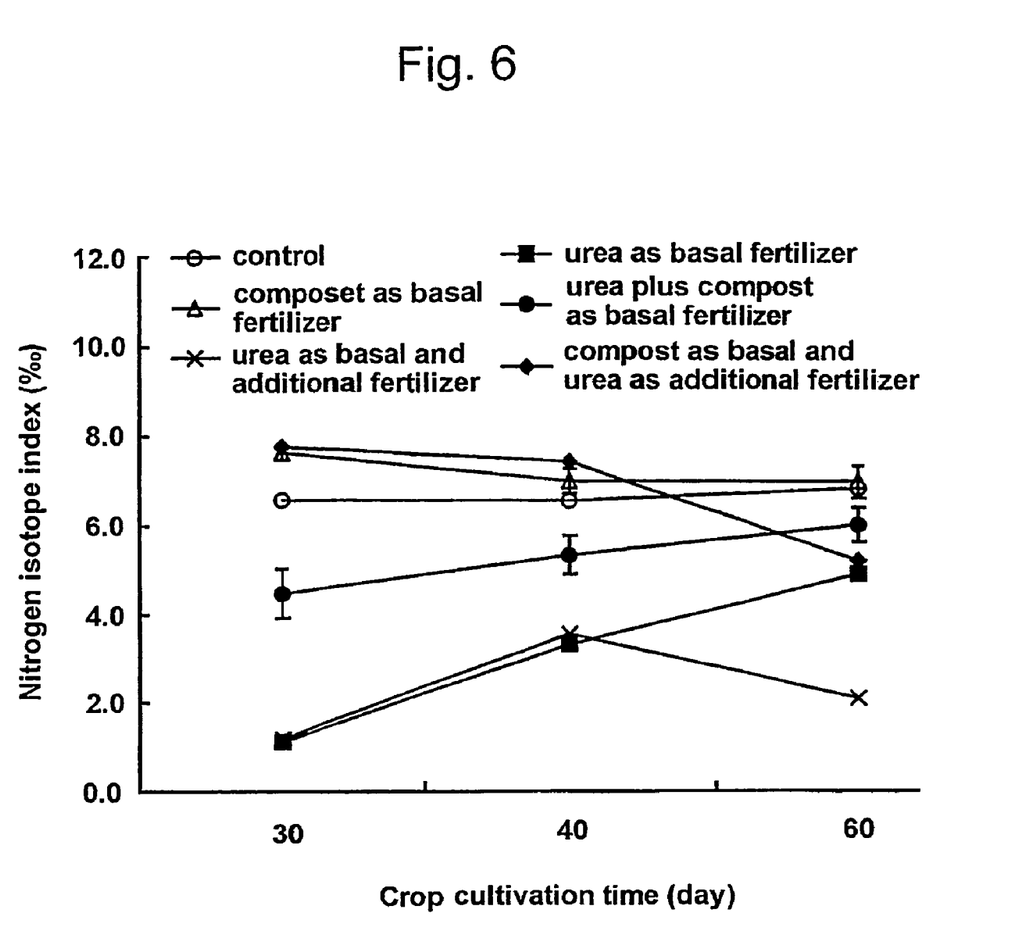
FIG. 6 illustrates a fluctuation in nitrogen isotope index value of a crop (a maize plant) during the cultivation period with time.

FIG. 6 illustrates a nitrogen isotope index value of whole nitrogen for a crop (a maize plant) during the cultivation period at appropriate intervals. As shown in FIG. 6, the nitrogen isotope index value for the control remained almost the same, and for the crop grown with only urea as a basal fertilizer, the nitrogen isotope index value for the crop continuously increased from 1.1±0.6‰ at the day 30$^{th}$ to 4.9±0.4‰ at the day 60$^{th}$.

On the other hand, for a crop grown with only compost as a basal fertilizer, the nitrogen isotope index decreased slightly from 7.7±0.2‰ at the day $30^{th}$ to 7.0±0.2‰ at the day $60^{th}$. For a crop grown with urea plus compost as a basal fertilizer, the nitrogen isotope index value increased from 4.5±0.6‰ at the day $30^{th}$ to 6.1±0.2‰ at the day $60^{th}$. On the other hand, for a crop grown with a urea as a basal and an additional fertilizer, the nitrogen isotope index value increased from 1.2±0.6‰ at the day $30^{th}$ to 3.6±0.4‰ at the day $40^{th}$, and then decreased to 2.1±0.4‰ at the $60^{th}$ day. For a crop grown with compost as a basal and urea as an additional fertilizer, the nitrogen isotope index value remained substantially the same at the $30^{th}$ (7.8±0.2‰) and $40^{th}$ day (7.5±0.3‰), and then decreased to 5.2±0.2‰ at the $60^{th}$ day by applying an additional fertilizer (at $40^{th}$ day of growth).

According to this Example, it is possible to determine that if the nitrogen isotope index exhibits an increasing trend during cultivation period with time, the crop is determined to be a conventional crop during the cultivation period of which a chemical fertilizer had been used as a sole fertilizer in the early growth period; if the nitrogen isotope index exhibits a decreasing trend after initial increasing trend during cultivation period with time, the crop is determined to be a conventional crop during the cultivation period of which a chemical fertilizer had been used as a basal fertilizer in the early growth period and as an additional fertilizer in the latter growth period; if the nitrogen isotope index exhibits almost no fluctuation or a slight decreasing trend during the cultivation period with time, the crop is determined to be an organic crop during the cultivation period of which an organic fertilizer was used as a sole fertilizer; and if the nitrogen isotope index exhibits a decreasing trend after initial insignificant fluctuating trend during the cultivation period with time, the crop is determined to be a conventional crop during the cultivation period of which an organic fertilizer was used as a basal fertilizer and a chemical fertilizer was used as an additional fertilizer.

EXAMPLE 6

In this Example, nitrogen isotope index values of a soil sample from a farmland and a crop harvested therefrom was measured and analysed.

Figure 7:
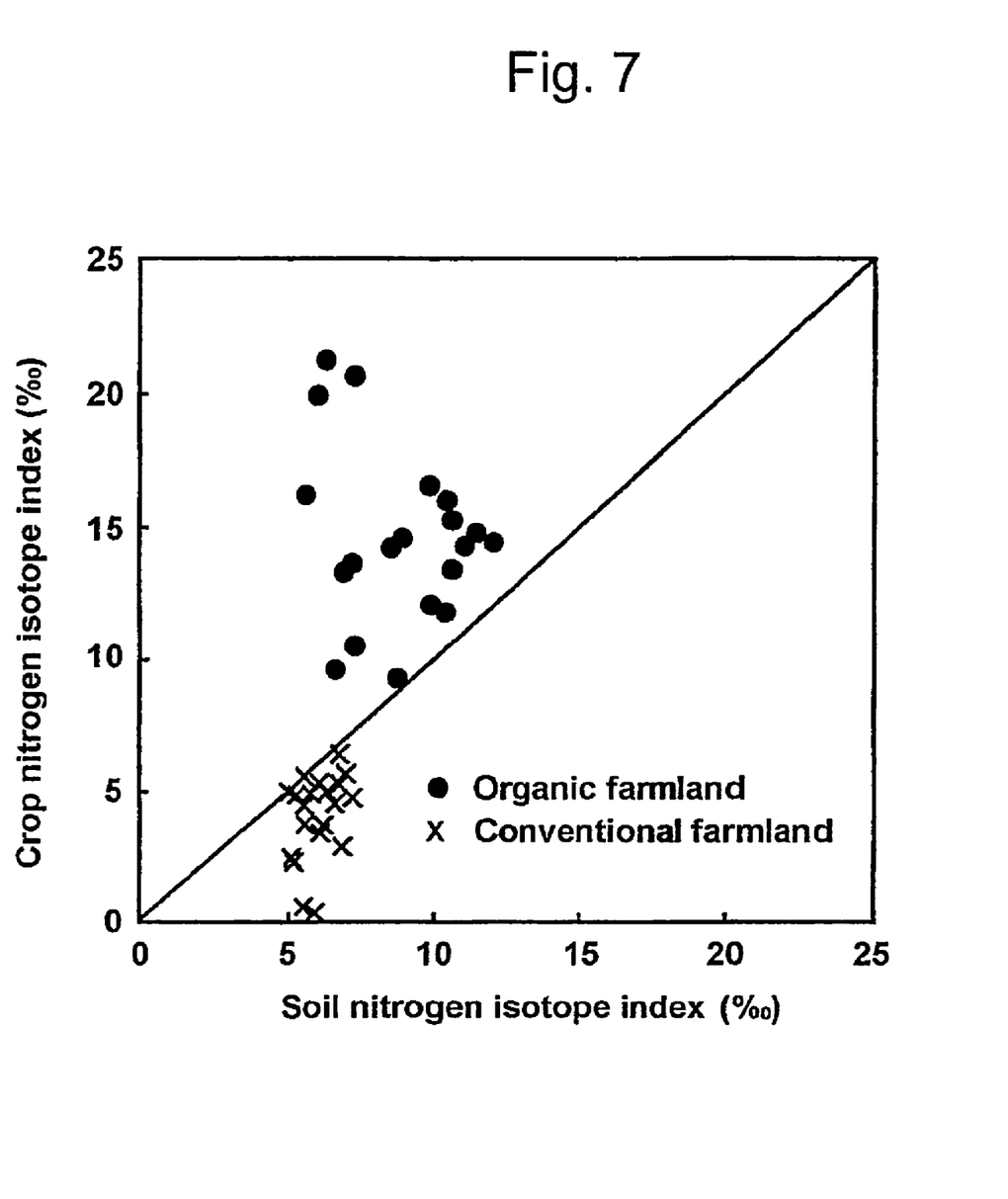
FIG. 7 illustrates a comparison of nitrogen isotope index values for an organic farmland and a conventional farmland with those of crops (a Chinese cabbage, a lettuce, a spinach, a sesame, a cucumber, a eggplant, a red pepper, a cabbage, a *Perilla japonica*) grown and harvested therefrom.

The kind of crop, a cultivation period, use and amount of a fertilizer were the same way as in the Example 4(2) and method for measuring a nitrogen isotope was carried out in the same as in the Example 2 and 4(2) since the data used in this Example was those of Example 2 for the soil and those of Example 4(2) for the crop. FIG. 7 illustrates a comparison of nitrogen isotope index values for an organic farmland and a conventional farmland with those of crop (a Chinese cabbage, a lettuce, a spinach, a sesame, a cucumber, a eggplant, a red pepper, a cabbage, a *Perilla japonica*) grown and harvested therefrom. As shown in FIG. 7, where a crop had been grown in a conventional farmland, a nitrogen isotope index of whole nitrogen in a crop sample harvested therefrom was lower than those of the soil of the conventional farmland, while where a crop was grown in an organic farmland, a nitrogen isotope index of whole nitrogen in a crop sample harvested therefrom was higher than those of the soil of the conventional farmland.

According to the results of this Example, it was found that if the nitrogen isotope index of the crop is lower than the nitrogen isotope index of the soil of the conventional farmland, the crop may be determined to be a conventional crop or the farmland may be determined to be a conventional farmland; and if the nitrogen isotope index of the crop is higher than the nitrogen isotope index of the soil of the conventional farmland, the crop may be determined to be an organic crop or the farmland may be determined to be an organic farmland.

According to the present invention, it is possible to discriminate an organic farmland from a conventional farmland by using a nitrogen isotope index of a soil sample.

According to the present invention, it is also possible to discriminate an organic crop from a conventional crop by using a nitrogen isotope index of a crop sample.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A method for discriminating an organic crop from a conventional crop, comprising:
   (a) measuring nitrogen isotope values in a crop sample at appropriate intervals during a single cultivation period;
   (b) calculating a pattern of nitrogen isotope index according to the formula (I) using the nitrogen isotope values of step (a):

$$\delta^{15}N = [R \text{ sample}/R \text{ reference} - 1] \times 1,000 \quad (I)$$

wherein $\delta^{15}N$ is a nitrogen isotope index, R sample and reference are $^{15}N/(^{15}N+^{14}N)$ ratio of sample and reference, respectively; and
   (c) determining whether the crop belongs to an organic crop or a conventional crop wherein:
      (i) if the nitrogen isotope index exhibits an increasing trend during the cultivation period with time, the crop is determined to be a conventional crop during the cultivation period of which a chemical fertilizer had been used as a sole fertilizer in the early growth period;
      (ii) if the nitrogen isotope index exhibits a decreasing trend after initial increasing trend, the crop is determined to be a conventional crop during the cultivation period of which a chemical fertilizer had been used as a basal fertilizer in the early growth period and as an additional fertilizer in the latter growth period;
      (iii) if the nitrogen isotope index exhibits almost insignificant fluctuations or a slight decreasing trend during the cultivation period with time, the crop is determined to be an organic crop during the cultivation period of which an organic fertilizer had been used as a sole fertilizer; or
      (iv) if the nitrogen isotope index exhibits a decreasing trend after initial insignificant fluctuating trend during the cultivation period with time, the crop is determined to be a conventional crop during the cultivation period of which an organic fertilizer had been used as a basal fertilizer in the early growth period and a chemical fertilizer had been used as an additional fertilizer in the latter growth period.

2. The method according to claim 1, wherein the crop is leaf vegetables.

3. The method according to claim 1, wherein the crop is selected from the group consisting of a Chinese cabbage, greens for picking, a *Brassica campestris* (a Chinese spinach-like green vegetable), a cabbage, a cauliflower, a broccoli, a Brussels sprout, an onion, a Welsh onion, a garlic, a scallion, a leek, an asparagus, a lettuce, a green for salad (which is called Saladana in Japan), a celery, a spinach, a crown daisy, a parsley, a trefoil (which is called Mitsuba in Japan and is useful as herb), a dropwort, an udo (which is an Aralia cordata), a Japanese ginger, a Japanese butterbur and a labiate.

* * * * *